US012281344B2

(12) United States Patent
Holmgren et al.

(10) Patent No.: US 12,281,344 B2
(45) Date of Patent: Apr. 22, 2025

(54) INTEGRATED GAS FERMENTATION

(71) Applicant: LanzaTech, Inc., Skokie, IL (US)

(72) Inventors: Jennifer Rosa Holmgren, Skokie, IL (US); Sean Alex Rollag, Chicago, IL (US); Richard Russell Rosin, Glencoe, IL (US); Taylor Craig Schulz, Chicago, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 18/674,362

(22) Filed: May 24, 2024

(65) Prior Publication Data

US 2024/0401089 A1 Dec. 5, 2024

Related U.S. Application Data

(60) Provisional application No. 63/471,190, filed on Jun. 5, 2023.

(51) Int. Cl.
| | |
|---|---|
| *C12P 7/08* | (2006.01) |
| *C12N 1/20* | (2006.01) |
| *C12P 5/00* | (2006.01) |
| *C12P 5/02* | (2006.01) |
| *C12P 7/42* | (2006.01) |
| *C12P 7/44* | (2006.01) |
| *C12R 1/02* | (2006.01) |
| *C12R 1/145* | (2006.01) |
| *C12R 1/26* | (2006.01) |

(52) U.S. Cl.
CPC ............... *C12P 7/08* (2013.01); *C12N 1/205* (2021.05); *C12P 5/007* (2013.01); *C12P 5/026* (2013.01); *C12P 7/42* (2013.01); *C12P 7/44* (2013.01); *C12R 2001/02* (2021.05); *C12R 2001/145* (2021.05); *C12R 2001/26* (2021.05)

(58) Field of Classification Search
CPC .................................................... C12P 7/08
See application file for complete search history.

(56) References Cited

U.S. PATENT DOCUMENTS

| | | |
|---|---|---|
| 1,128,549 A | 2/1915 | Tait |
| 1,408,091 A | 2/1922 | Edward |
| 2,099,090 A | 11/1937 | Webb |
| 2,405,986 A | 8/1946 | Sullivan |
| 3,020,708 A | 2/1962 | Mahan |
| 3,102,875 A | 9/1963 | Heiss |
| 4,692,168 A | 9/1987 | Dotson |
| 5,173,429 A | 12/1992 | Gaddy |
| 5,593,886 A | 1/1997 | Gaddy |
| 6,368,819 B1 | 4/2002 | Gaddy |
| 6,811,769 B2 | 11/2004 | Watanabe |
| 7,972,824 B2 | 7/2011 | Simpson |
| 8,293,509 B2 | 10/2012 | Simpson |
| 8,658,408 B2 | 2/2014 | Simpson |
| 8,900,836 B2 | 12/2014 | Simpson |
| 9,068,202 B2 | 6/2015 | Tran |
| 9,284,564 B2 | 3/2016 | Mueller |
| 9,347,076 B2 | 5/2016 | Liew |
| 9,359,611 B2 | 6/2016 | Koepke |
| 9,410,130 B2 | 8/2016 | Koepke |
| 9,738,875 B2 | 8/2017 | Koepke |
| 9,890,384 B2 | 2/2018 | Mueller |
| 9,994,878 B2 | 6/2018 | Koepke |
| 10,174,303 B2 | 1/2019 | Behrendorff |
| 10,494,600 B2 | 12/2019 | Heijstra |
| 10,590,406 B2 | 3/2020 | Koepke |
| 10,856,560 B2 | 12/2020 | Simpson |
| 10,913,958 B2 | 2/2021 | Koepke |
| 11,555,209 B2 | 1/2023 | Koepke |
| 2011/0244538 A1 | 10/2011 | Trevethick |
| 2012/0045807 A1 | 2/2012 | Simpson |
| 2012/0121468 A1 | 5/2012 | Tsangaris |
| 2013/0157322 A1 | 6/2013 | Simpson |
| 2013/0230609 A1 | 9/2013 | Modak |
| 2021/0292732 A1 | 9/2021 | Liew |

(Continued)

FOREIGN PATENT DOCUMENTS

| | | |
|---|---|---|
| EP | 117309 A1 | 9/1984 |
| WO | 1992008555 A1 | 5/1992 |

(Continued)

OTHER PUBLICATIONS

Abrini et al., "Clostridium autoethanogenum, sp. Nov., an anaerobic bacterium that produces ethanol from carbon monoxide," Arch of Microbiol (1994) 161, p. 345-351.

Chi et al. (2011), Oleaginous yeast Cryptococcus curvatus culture with dark fermentation hydrogen production effluent as feedstock for microbial lipid production, International Journal of Hydrogen Energy, 36:9542-9550.

Demler et al., "Reaction Engineering Analysis of Hydrogenotrophic Production of Acetic Acid by Acetobacterium woodii," Biotechnology and Bioengineering, vol. 108, No. 2, Feb. 2011, p. 470-474.

Klasson et al., "Bioconversion of synthesis gas into liquid or gaseous fuels," Enzyme and Microb. Technol., Aug. 1992, vol. 14, p. 602-608.

Klasson et al., "Bioreactors for synthesis gas fermentations," Resources, Conservation and Recycling, 5 (1991) p. 145-165.

Klasson, et al.(1991), Bioreactor design for synthesis gas fermentations, Fuel, 1991, vol. 70, p. 605-614.

(Continued)

Primary Examiner — Tekchand Saidha

(57) ABSTRACT

Integrated process for providing multiple raw materials to a downstream operation to generate an article of manufacture. Pyrolysis, torrefaction, reforming, partial oxidation, and/or gasification is integrated with gas fermentation. Integrated process converts carbon sources that would otherwise be vented to the atmosphere or discarded as waste to a fermentation product and one or more byproducts, which in turn are provided to a downstream operation to generate an article of manufacture. In certain aspects, the fermentation product may be ethanol, isoprene, butane diol, ethylene. In certain aspects, the byproduct may be metal, metal oxide, char, silica, and or steel. The downstream operation to generate an article of manufacture may be an operation to generate plastic products, rubber products, textiles, clothes, and the like.

11 Claims, 1 Drawing Sheet

(56) References Cited

U.S. PATENT DOCUMENTS

| | | | |
|---|---|---|---|
| 2021/0371312 A1 | 12/2021 | Conrado | |
| 2022/0325227 A1* | 10/2022 | Conrado | .................. C12P 7/08 |

FOREIGN PATENT DOCUMENTS

| | | |
|---|---|---|
| WO | 1997010331 A1 | 3/1997 |
| WO | 9800558 A1 | 1/1998 |
| WO | 0068407 A1 | 11/2000 |
| WO | 0208438 A2 | 1/2002 |
| WO | 2006088491 A2 | 8/2006 |
| WO | 2007115157 A2 | 10/2007 |
| WO | 2008115080 A1 | 9/2008 |
| WO | 2010056463 A2 | 5/2010 |
| WO | 2011034887 A2 | 3/2011 |
| WO | 2014100851 A1 | 7/2014 |
| WO | 2015059656 A1 | 4/2015 |
| WO | 2015073854 A2 | 5/2015 |
| WO | 2017161387 A1 | 9/2017 |

OTHER PUBLICATIONS

Lewis et al., "Making the connection: conversion of biomass-generated producer gas to ethanol," Proceedings Bioenergy 2002 Conference, p. 1-8.

Liou et al., "Clostridium carboxidivorans sp. nov., a solvent-producing clostridium isolated from an agricultural settling lagoon, and reclassification of the acetogen Clostridium scatologenes strain SL1 as Clostridium drakei sp. nov.," International Journal of Systematic and Evolutionary Microbiology (2005), 55, 2085-2091.

Martin et al., "Dissimilation of Carbon Monoxide to Acetic Acid by Glucose-Limited Cultures of Clostridium thermoaceticum," Applied and Environmental Microbiology, vol. 49, No. 6, Jun. 1985, p. 1412-1417.

Najafpour et al., "Ethanol and acetate synthesis from waste gas using batch culture of Clostridium ljungdahlii," Enzyme and Microbial Technology, 38 (2006) p. 223-228.

Sakai et al., "Ethanol production from H2 and CO2 by a newly isolated thermophilic bacterium, Moorella sp. HUC22-1," Biotechnology Letters 26: pp. 1607-1612, 2004.

Sipma et al., "Microbial CO Conversions with Applications in Synthesis Gas Purification and Bio-Desulfurization," Critical Reviews in Biotechnology, vol. 26. p. 41-65, 2006.

Svetlichny et al., "Carboxydothermus hydrogenoformans gen. nov., sp. Nov., a CO-utilizing Thermophilic Anaerobic Bacterium from Hydrothermal Environments of Kunashir Island," System. Allp. Microbiol. 14, 254-260 (1991).

Vega et al., "Study of Gaseous Substrate Fermentation: Carbon Monoxide Conversion to Acetate. 2. Continuous Culture," Biotechnology and Bioengineering, vol. 34, p. 785-793 (1989).

Vega et al., "Study of gaseous substrate fermentations: Carbon monoxide conversion to acetate. 1. Batch culture," Biotechnology and Bioengineering, vol. 34, p. 774-784 (1989).

Vega et al., "Design of Bioreactors for Coal Synthesis Gas Fermentations," Resources, Conservation and Recycling, 3 (1990) p. 149-160.

International Search Report for International Patent Application PCT/US2024/031088, Korean Intellectual Property Office, Sep. 13, 2024, 10 pages.

* cited by examiner

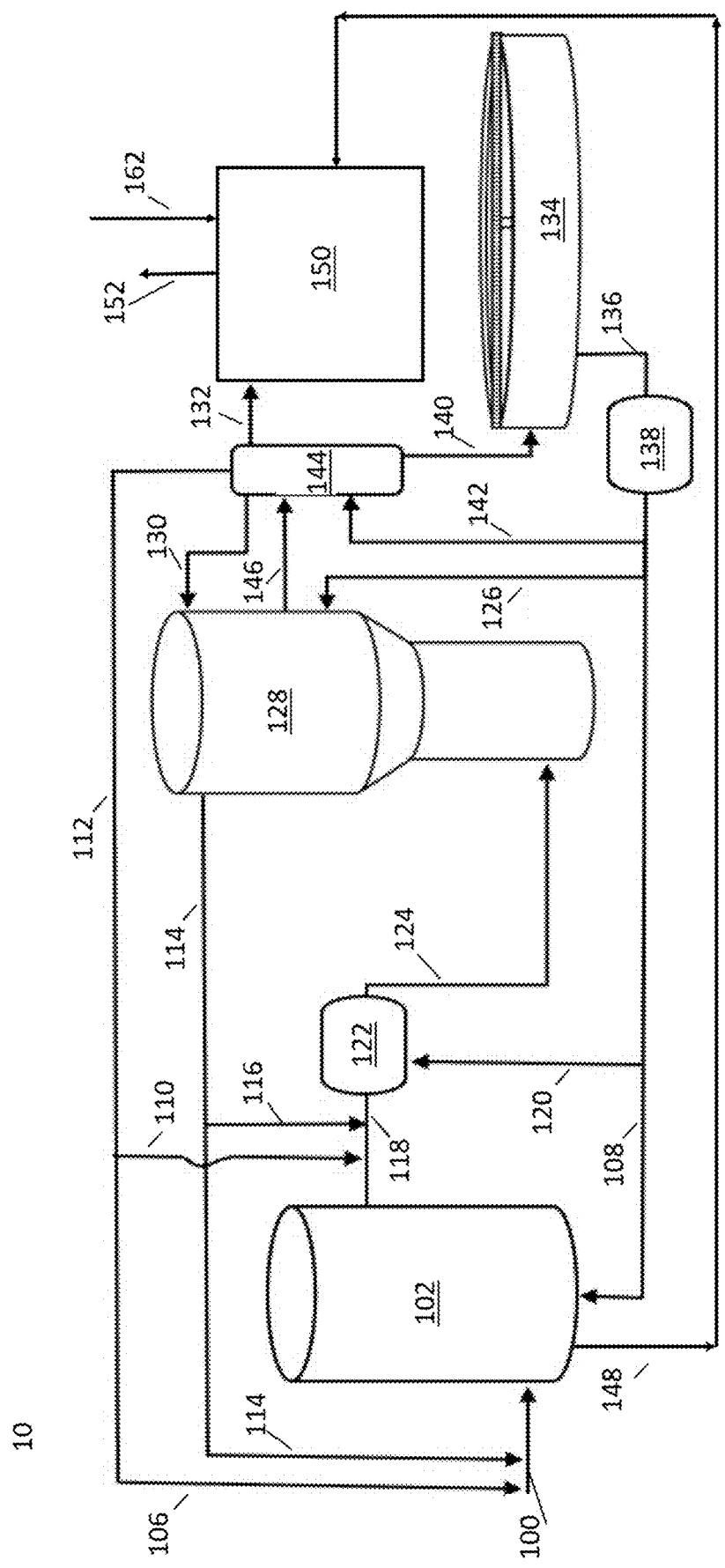

INTEGRATED GAS FERMENTATION

CROSS REFERENCE TO RELATED APPLICATIONS

This application claims the benefit of U.S. Provisional Patent Application No. 63/471,190, filed on Jun. 5, 2023, the entirety of which is incorporated herein by reference.

FIELD

This disclosure relates to an integrated process of feedstock preparation and gas fermentation wherein a material generated during feedstock preparation is provided to a downstream operation to increase recycling of valuable material. Such material produced as a byproduct of the feedstock preparation may otherwise be discarded. More specifically, the present disclosure relates to systems and methods for an integrated process where partial oxidation, pyrolysis torrefaction, reforming, or gasification is used to provide feedstock to a gas fermentation process and where both a product of gas fermentation and a at least one byproduct of the feedstock preparation process provided to a common downstream operation to produce an article of manufacture.

BACKGROUND

The following discussion is provided to aid the reader in understanding the disclosure and is not admitted to describe or constitute prior art thereto.

Gas fermentation processes can be used to generate target materials from gas substrates or other input materials, particularly carbon-based materials. For example, particular biological systems can be used to perform gas fermentation.

Gas fermentation involves a gas stream of carbon monoxide, carbon dioxide, and or hydrogen provided to a bioreactor housing a microorganism biocatalyst. Although industrial processes can output gases that have significant amounts of carbon-based materials such as carbon dioxide, many other sources of carbon are available. Solid and liquid sources of carbon may be processed in a feedstock preparation process to provide synthesis gas, commonly called syngas which may in turn become feedstock to the gas fermentation process. The feedstock preparation process, which is processing to provide syngas, involves partial oxidation, torrefaction, reforming, pyrolysis or gasification. By products may be formed in addition to the syngas. Utilizing the byproducts further enhances the benefits of a gas fermentation overall process.

There exists a need to increase overall value which is particularly enhanced when the gas fermentation product and one or more byproducts from the feedstock preparation process are provided to a downstream operation to produce an article of manufacture. What might otherwise be waste is instead provided for utilization along with the gas fermentation product to a downstream operation.

SUMMARY

In a first aspect, the present disclosure provides an integrated process and system comprising: a) processing at least one material comprising carbon atoms, in a partial oxidation, pyrolysis, torrefaction, reforming, or gasification process, to produce a raw syngas steam comprising at least carbon monoxide and carbon dioxide, and to produce at least one byproduct selected from a metal, metal oxide, silica, steel, and char; b) passing at least a portion of the syngas stream to a gas fermentation process comprising a bioreactor containing a C1-fixing microorganism in a liquid nutrient medium to produce at least one fermentation product; c) providing the at least one byproduct and the at least one fermentation product to a downstream operation to produce an article of manufacture.

In some embodiments, at least two byproducts are produced by the partial oxidation, pyrolysis, torrefaction, reforming, or gasification process and both byproducts are provided to the downstream operation to produce an article of manufacture.

In some embodiments, at least three byproducts are produced by the partial oxidation, pyrolysis, torrefaction, reforming, or gasification process and all three byproducts are provided for use in the downstream operation to produce an article of manufacture.

In some embodiments, at least four byproducts are produced by the partial oxidation, pyrolysis, torrefaction, reforming, or gasification process and all four byproducts are provided for use in the downstream operation to produce an article of manufacture.

In some embodiments, the metal or metal oxide comprises zinc.

In some embodiments, the process further comprises processing the char to generate carbon black prior to being provided for use in the downstream operation to produce an article of manufacture.

In some embodiments, the at least one material comprises a whole tire or at least a portion of a tire.

In some embodiments, the tire is an end of life tire.

In some embodiments, the downstream operation to produce an article of manufacture is at least one step of a tire production process.

In some embodiments, two or more byproducts are produced by the partial oxidation, pyrolysis, torrefaction, reforming, or gasification process and the two or more byproducts are provided to the same or different steps of a production process to manufacture a tire.

In some embodiments, the at least one material comprises a natural or synthetic rubber containing material.

In some embodiments, the downstream operation to produce an article of manufacture is at least one step of a production process to manufacture a rubber containing article.

In some embodiments, two or more byproducts are produced by the partial oxidation, pyrolysis, torrefaction, reforming, or gasification process and the two or more byproducts are provided to the same or different steps of the production process to manufacture a rubber containing article.

In some embodiments, the fermentation product is selected from selected from an alcohol, an acid, a diacid, an alkene, a terpene, an isoprene, and alkyne.

In some embodiments, the C1-fixing microorganism is an acetogenic carboxydotrophic microorganism.

In some embodiments, the gas fermentation product and the at least one byproduct are provided to the same or different steps of the downstream operation to produce an article of manufacture.

In some embodiments, the at least one material is selected from coal, refinery residues, petroleum coke, biomass, lignocellulosic material, black liquor, municipal solid waste, municipal liquid waste, industrial solid waste, industrial liquid waste, refuse derived fuel, sewerage, sewerage sludge, sludge from wastewater treatment, landfill gas, biogas, tires including end of life tires, or combinations thereof.

In some embodiments, the material is selected from unsorted landfill waste, sorted landfill waste, tires, plastics, fibers, microbial biomass, waste wood, agriculture waste, forest waste, or combinations thereof.

In some embodiments the microorganism is selected from a genus of *Clostridium, Moorella, Carboxydothermus, Ruminococcus, Acetobacterium, Eubacterium, Butyribacterium, Oxobacter, Methanosarcina, Methanosarcina, Desulfotomaculum*, and *Cupriavidus*.

BRIEF DESCRIPTION OF THE DRAWINGS

The FIGURE has been simplified by the deletion of a large number of apparatuses customarily employed in a process/system of this nature, such as vessel internals, temperature and pressure control systems, flow control valves, recycle pumps and the like, which are not specifically required to illustrate the performance of the invention. Furthermore, the illustration of the process of this invention in the embodiment of a specific drawing is not intended to limit the disclosure to specific embodiments. Some embodiments may be described by reference to the process configuration shown in the FIGURE, which relates to both apparatus and processes to carry out the disclosure. Any reference to a process step includes reference to an apparatus unit or equipment that is suitable to carry out the step, and vice-versa.

The FIGURE is an overview of the piping and associated components of an embodiment of an integrated feedstock preparation and gas fermentation process.

DETAILED DESCRIPTION

The present disclosure provides processes and systems for improving value of integrated feedstock preparation and gas fermentation operations by providing multiple needed raw materials to a downstream operation to produce an article of manufacture. The integrated process addresses a wide variety of carbon sources suitable for microbial gas fermentation that converts carbon sources that would otherwise be discarded to one or more products. Byproducts generated in the feedstock preparation for gas fermentation are provided, along with the gas fermentation product for use in a downstream operation to produce an article of manufacture. More specifically, byproduct(s) from a feedstock preparation involving, pyrolysis, torrefaction, reforming, partial oxidation, or gasification are provided to a downstream operation to produce an article of manufacture along with the product of the gas fermentation process. Therefore, a greater amount of the initial feedstock material is recycled and available for use in the manufacture of a new article. A particular application is in the feedstock containing an article of manufacture that is the article of manufacture as produced in the downstream operation.

Definitions

It is to be understood that the terminology used herein is for the purpose of describing particular embodiments only and is not intended to be limiting.

Technical and scientific terms used herein have the meanings commonly understood by one of ordinary skill in the art, unless otherwise defined. Unless otherwise specified, materials and/or methodologies known to those of ordinary skill in the art can be utilized in carrying out the methods described herein, based on the guidance provided herein.

As used herein, the singular terms "a," "an," and "the" include plural referents unless the context clearly dictates otherwise. Reference to an object in the singular is not intended to mean "one and only one" unless explicitly so stated, but rather "one or more."

As used herein, "about" when used with a numerical value means the numerical value stated as well as plus or minus 10% of the numerical value. For example, "about 10" should be understood as both "10" and "9-11."

Also as used herein, "and/or" refers to and encompasses any and all possible combinations of one or more of the associated listed items, as well as the lack of combinations when interpreted in the alternative ("or").

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "carbon capture" as used herein refers to the fixation and utilization of carbon including carbon from $CO_2$, CO, and/or $CH_4$ from a stream comprising $CO_2$, CO, and/or $CH_4$ and converting the $CO_2$, CO, and/or $CH_4$ into useful products.

The term "substrate comprising carbon monoxide" and like terms should be understood to include any substrate in which carbon monoxide is available to one or more strains of bacteria for growth and/or fermentation, for example.

The term "gaseous substrates comprising carbon monoxide" includes any gas which contains carbon monoxide. The gaseous substrate will typically contain a significant proportion of CO, preferably at least about 5 vol.-% to about 100 vol.-% CO.

The term "C1 carbon" and like terms should be understood to refer to carbon sources that are suitable for use by a C1 fixing microorganism, particularly those of the gas fermentation process disclosed herein. C1 carbon may include, but should not be limited to, carbon monoxide (CO), carbon dioxide ($CO_2$), and methane ($CH_4$), methanol ($CH_3OH$), and formate (HCOOH).

The term "substrate comprising carbon dioxide" and like terms should be understood to include any substrate in which carbon dioxide is available to one or more strains of bacteria for growth and/or fermentation, for example.

The term "gaseous substrates comprising carbon dioxide" includes any gas which contains carbon dioxide. Some gaseous substrates contain a significant proportion of $CO_2$, such as at least about 50 vol.-% to about 100 vol.-% $CO_2$, while other gaseous substrates that contain $CO_2$ are more dilute and contain from about 5 vol.-% to about 50 vol.-% Advantageously the present disclosure reduces energy requirement for gaseous substrates comprising from about 5 vol.-% to about 20 vol.-% carbon dioxide thereby allowing dilute $CO_2$ containing streams to be processed economically by gas fermentation.

The term "bioreactor" includes a fermentation device consisting of one or more vessels and/or towers or piping arrangements, which includes the continuous stirred tank reactor (CSTR), immobilized cell reactor (ICR), trickle bed reactor (TBR), bubble column, gas lift fermenter, loop reactors, membrane reactor such as hollow fiber membrane bioreactor (HFMBR), static mixer, high throughput, or other vessel or other device suitable for gas-liquid contact.

The term "co-substrate" refers to a substance that, while not necessarily being the primary energy and material source for product synthesis, can be utilized for product synthesis when added to another substrate, such as the primary substrate.

The term "directly", as used in relation to the passing of industrial off or gases to a bioreactor, is used to mean that no or minimal processing or treatment steps, such as cooling and particulate removal are performed on the gases prior to them entering the bioreactor (note: an oxygen removal step may be required for anaerobic fermentation).

The terms "fermenting," "fermentation process," "fermentation reaction," and like terms as used herein, are intended to encompass both the growth phase and product biosynthesis phase of the process. As is described further herein, in some embodiments the bioreactor may comprise a primary bioreactor and a secondary bioreactor.

The term "nutrient medium" as used herein should be understood as the solution added to the fermentation broth containing nutrients and other components appropriate for the growth of the microorganism culture.

The terms "primary bioreactor" or "first reactor" as used herein this term is intended to encompass one or more reactors that may be connected in series or parallel with a secondary bioreactor. The primary bioreactors generally use anaerobic or aerobic fermentation to produce a product (e.g., ethylene, ethanol, acetate, etc.) from a gaseous substrate.

The terms "secondary bioreactor" or "second reactor" as used herein are intended to encompass any number of further bioreactors that may be connected in series or in parallel with the primary bioreactors. Any one or more of these further bioreactors may also be connected to a further separator.

The term "stream" is used to refer to a flow of material into, through and away from one or more stages of a process, for example, the material that is fed to a bioreactor. The composition of the stream may vary as it passes through particular stages. For example, as a stream passes through the bioreactor.

The terms "feedstock" when used in the context of the stream flowing into a gas fermentation bioreactor (i.e., gas fermenter) or "gas fermentation feedstock" should be understood to encompass any material (solid, liquid, or gas) or stream that can provide a substrate and/or C1-carbon source to a gas fermenter or bioreactor either directly or after processing of the feedstock.

The term "waste gas" or "waste gas stream" may be used to refer to any gas stream that is either emitted directly, flared with no additional value capture, or combusted for energy recovery purposes.

The term "underutilized gas" or "underutilized gas stream" may be used to refer to any gas stream that may have greater value as a substrate to gas fermentation than a current use.

The terms "synthesis gas" or "syngas" refers to a gaseous mixture that contains at least one carbon source, such as carbon monoxide (CO), carbon dioxide ($CO_2$), or any combination thereof, and, optionally, hydrogen ($H_2$) that can used as a feedstock for the disclosed gas fermentation processes and can be produced from a wide range of carbonaceous material, both solid and liquid.

A. Disclosed Systems and Methods

For many industrial processes, emission of gases that contain carbon are commonplace. Industrial process operators may view flaring and venting carbon rich sources to the atmosphere or otherwise discarding them as traditional standard techniques. Many domestic and international governmental entities are placing tighter restrictions on the total amount of waste carbon that a particular site, complex, or entity is allowed to release into the atmosphere. Such restrictions are pushing industrial, commercial, and agricultural operators alike to pursue and implement expensive efficiency upgrades to perhaps already well-developed technologies within their respective fields.

Processes and systems in accordance with the present disclosure can be used to transform carbon in solid and liquid feedstocks by microbial gas fermentation systems to generate valuable products and divert carbon compounds from being treated as waste and for example incinerated to create emissions into the atmosphere. Currently, the primary product of gas fermentation is provided to downstream operations to produce articles of manufacture. The product of gas fermentation may be provided for use as an intermediate, a reactant, a solvent, an ingredient, or other such uses in the downstream operation. However, one or more byproducts of an integrated feedstock preparation and gas fermentation process may also be provided for use as an intermediate, a reactant, a solvent, an ingredient, or other such uses in the downstream operation. The more material from the integrated feedstock preparation and gas fermentation process that is provided to the downstream operation, the more value that is derived from the integrated feedstock preparation and gas fermentation process. Providing an increased amount of material for productive use results in less waste. Byproducts of the feedstock preparation to provide syngas to the gas fermentation may also be provided to downstream operations. The byproducts may be provided to the same downstream operation to which the gas fermentation product is provided. Further, the material provided to the feedstock preparation may be articles of the same type as being produced in the downstream operation, only that the articles used in the feedstock preparation are used, defective, or scrap articles whereas the downstream operation produces new articles.

Gas fermentation processes that are capable of converting various carbon sources into other products are rapidly becoming a desirable alternative for producers with excess carbon. Such processes allow companies or organizations to convert standard techniques that emit carbon into the atmosphere into a separate revenue stream by converting the waste or underutilized carbon into a marketable product. Moreover, the carbon that is converted into other products lowers the operator's total carbon output, potentially serving as a way for operators to maintain current outputs without conflicting with ever-tightening government regulations. Furthermore, tail gas from gas fermentation may be another source of $CO_2$ and purified to form a concentrated $CO_2$ stream thereby further reducing cost as compared to more traditional carbon capture and sequestration processes. The widespread adoption of gas fermentation processes could be improved by reducing the cost barriers through the use of additional material from the integrated process being available to downstream operations.

In one embodiment the substrate and/or C1 carbon source provides both the energy and the carbon source for the metabolic process of the biocatalyst, while in another embodiment, such as when $CO_2$ is the carbon source, depending upon the biocatalyst, a source of energy for the metabolic process is also provided. Typically, the source of energy for the metabolic process may be hydrogen. The hydrogen may be mixed with the C1 carbon source prior to the bioreactor of the gas fermentation system or may be independently supplied to the bioreactor.

The substrate and or C1 carbon source may be in the form of a solid or liquid material which may be first processed in a preliminary step of the overall integrated gas fermentation process to generate synthesis gas known as syngas which in turn is provided to the bioreactor of the gas fermentation system. The preliminary step to generate syngas may involve pyrolysis, partial oxidation, plasma, torrefaction, reforming, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of landfill gas, gasification of biogas such as when biogas is added to enhance gasification of another material, and gasification of tires including end of life tires. Examples of partial oxidation processes include thermal and catalytic partial oxidation processes, catalytic partial oxidation of natural gas, partial oxidation of hydrocarbons, partial oxidation of biogas, partial oxidation of landfill gas, or partial oxidation of pyrolysis off-gas. Examples of municipal solid waste include tires, plastics, refuse derived fuel, and fibers such as in shoes, apparel, and textiles. Municipal solid waste may be simply landfill-type waste and may be sorted or unsorted. Examples of biomass may include lignocellulosic material and microbial biomass. Lignocellulosic material may include agriculture waste and forest waste.

The microorganism of the disclosure may be cultured with the gaseous substrate to produce one or more target products. Target product(s) may be selected from an alcohol, an acid, a diacid, an alkene, a terpene, an isoprene, and alkyne. For instance, the microorganism of the disclosure may produce or may be engineered to produce ethanol, acetate, 1-butanol, 2,3-butanediol, lactate, butene, butadiene, methyl ethyl ketone (2-butanone), ethylene, acetone, isopropanol, lipids, 3-hydroxypropionate (3-HP), terpenes, including isoprene, fatty acids, 2-butanol, 1,2-propanediol, 1 propanol, 1 hexanol, 1 octanol, chorismate-derived products, 3hydroxybutyrate, 1,3 butanediol, 2-hydroxyisobutyrate or 2-hydroxyisobutyric acid, isobutylene, adipic acid, 1,3 hexanediol, 3-methyl-2-butanol, 2-buten-1-ol, isovalerate, isoamyl alcohol, and/or monoethylene glycol in addition to ethylene. In certain embodiments, microbial biomass itself may be considered a product.

Referring now to the FIGURE, which illustrates an integrated gas fermentation (GF) system 10 having a feedstock preparation zone within the system 10, the FIGURE shows an enlarged gas fermentation process including the feedstock preparation as gasification process 102, a gas fermentation zone 128, a product recovery zone 144, and an optional wastewater treatment zone 134, and a downstream operation to produce an article of manufacture 150. Feedstock preparation gasification process 102 receives feedstock 100, which may be any suitable material capable of being gasified to produce syngas stream 118. In various instances, feedstock 100 may be comprised at least partially of sorted and/or unsorted industrial or municipal solid waste including tires and end of life tires. In other instances, the feedstock 100 is comprised at least partially of forest and/or agricultural waste. In particular embodiments, feedstock 100 is comprised of any combination of two or more of the following: sorted municipal or industrial solid waste, unsorted municipal or industrial solid waste, tires including end of life tires, rubber containing material, forest waste, agricultural waste, or other solid or liquid waste from the refining or chemical process integrated with the enlarged gas fermentation process. In particular embodiments, a combination of two or more materials are processed together as one material alone may be difficult to process. Integration internal to the enlarged fermentation process may provide for at least one effluent from the gas fermentation zone 128, at least one effluent from the product recovery zone 144, and or at least one effluent from the wastewater treatment zone 134 being used as gasification feed.

Gasification zone 102 produces syngas as substrate for gas fermentation zone 128. In some embodiments, syngas 118 produced in the gasification zone 102 by the gasification process, or gas obtained from another source and combined with the syngas 118 contains one or more constituent that needs to be removed and/or converted. Typical constituents found in the syngas stream 118 that may need to be removed and/or converted include, but are not limited to, sulfur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars. These constituents may be removed by one or more removal zones 122 positioned between gasification zone 102a and gas fermentation zone 128. Removal zone 122 may comprise one or more of the following modules: hydrolysis module, acid gas removal module, deoxygenation module, catalytic hydrogenation module, particulate removal module, chloride removal module, tar removal module, and hydrogen cyanide polishing module. Two or more modules may be combined into a single module performing the same functions. The functions of all modules may be combined into a single unit with the selection of an appropriate catalyst, such as for example U.S. Pat. No. 11,441,116. When incorporating removal process 122, at least a portion of syngas 118 from gasification zone 102a is passed to removal process 122 to remove and/or convert at least a portion of at least one constituent found in syngas stream 118. Removal zone 122 may operate to bring the constituent(s) within allowable levels to produce a treated stream 124 suitable for fermentation by in gas fermentation zone 128.

Fermentation process 128 employs at least one C1-fixing microorganism in a liquid nutrient media to ferment a feedstock gas, or syngas stream 124 and produce one or more products. The C1-fixing microorganism in fermentation process 128 may be a carboxydotrophic bacterium, or an acetogenic carboxydotrophic bacterium. In particular embodiments, the C1-fixing microorganism may be an acetogenic carboxydotrophic bacterium. The C1-fixing microorganism may be selected from the group comprising *Moorella, Clostridium, Ruminococcus, Acetobacterium, Eubacterium, Butyribacterium, Oxobacter, Methanosarcina, Methanosarcina, Cupriavidus* and *Desulfotomaculum*. In various embodiments, the acetogenic carboxydotrophic bacterium is *Clostridium autoethanogenum*.

The one or more products produced in fermentation zone 128 are removed and/or separated from the fermentation broth in product recovery zone 144. Product recovery zone 144 separates and removes one or more product(s) 132 and produces at least one effluent 142, 130, 112, which comprise reduced amounts of at least one product. Product depleted effluent may be sent via a conduit 142 to wastewater treatment zone 134 to produce at least one effluent 136, which may be recycled to the gasification process 102*a* and/or the fermentation process 128.

In at least one embodiment, an effluent from fermentation zone 128 is tail gas containing gas generated by the fermentation, inert gas, and or unmetabolized substrate. At least a portion of this tail gas may be passed via a conduit 114 to gasification zone 102 to be used as part of feedstock 100. At least a portion of the tail gas may be sent via conduit 114 and a conduit 116 to syngas 118, an effluent of gasification zone 102, to quench syngas stream 118. At least a portion of the tail gas may be passed outside of the enlarged gas fermentation process.

In at least one embodiment, the effluent from fermentation zone 128 is fermentation broth. At least a portion of the fermentation broth may be sent via conduit 146 to product recovery zone 144. In at least one embodiment, product recovery zone 144 separates at least a portion of the microbial biomass from the fermentation broth. In various instances, at least a portion of the microbial biomass that is separated from the fermentation broth is recycled to the fermentation zone 128 via a conduit 130. In various instances, at least a portion of the microbial biomass separated from the fermentation broth is passed via a conduit 106 to optional gasification zone 102 for use as part of feedstock 100. In certain instances, fermentation zone 128 produces fusel oil which may also be recovered in product recovery zone 144 through any suitable means such as within the rectification column of a distillation system. In at least one embodiment, at least a portion of the fusel oil from the product recovery zone 144 is used as a heating source for one or more zones or elsewhere external to the enlarged process.

In various instances, at least a portion of a wastewater stream, comprising fermentation broth, which may contain microbial biomass from fermentation zone 128 may be passed to optional gasification zone 102, without being passed to product recovery zone 144.

In instances where the fermentation broth is processed by the product recovery process 144, at least a portion of the microbial biomass depleted water, produced through the removal of microbial biomass from the fermentation broth, may be returned to fermentation zone 128 via a conduit 130 and/or sent via a conduit 112 to optional gasification zone 102*a*. At least a portion of the microbial biomass depleted water may be passed via conduit 106 to optional gasification zone 102*a* to be used as part of feedstock 100. At least a portion of the microbial biomass depleted water may be passed via conduit 110 to quench syngas stream 118. At least a portion of the effluent from product recovery zone 144 may be passed via conduit 140 to wastewater treatment zone 134. The effluent from product recovery zone 144 may comprise reduced amounts of product and/or microbial biomass.

Wastewater treatment zone 134 receives and treats effluent from one or more zones to produce clarified water. The clarified water may be passed or recycled via a conduit 136 to one or more zones. For example, at least a portion of the clarified water may be passed via conduit 126 to the fermentation zone, at least a portion of the clarified water may be passed to optional gasification zone 102 via conduit 108 to be used as part of feedstock 100 and or via conduit 120 to quench syngas stream 118 in quench zone 122. In certain instances, the wastewater treatment process 134 generates microbial biomass as part of the treatment process. At least a portion of this microbial biomass may be passed via conduit 108 to the gasification zone 102 for use as part of feedstock 100. Wastewater treatment zone 134, as a by-product of treating microbial biomass, produces biogas. At least a portion of the biogas may be passed via conduit 136 to gasification zone 102*a* to be used as part of feedstock 100 and or via a conduit 120 to quench syngas stream 118.

Optional wastewater treatment effluent removal unit 138 is positioned downstream of wastewater treatment zone 134. At least a portion of biogas from wastewater treatment zone 134 may be passed to removal unit 138 to remove and/or convert at least a portion of at least one constituent found in the biogas stream. Removal unit 138 operates to lower the concentration of constituents to within predetermined allowable levels and produce a treated stream 142, 126, 120, and/or 108 suitable to be used by the subsequent one or more zones 144, 128, 122, and/or 102*a*, respectively.

Gas fermentation product 132 is provided to downstream operation 150. Downstream operation 150 is an operation to produce an article of manufacture 152. Other feedstock(s) 162 may be provided to downstream operation 150. Gas fermentation product 132 may be a reactant, an intermediate, an ingredient, a production aide, or of other use in downstream operation 150. Feedstock preparation, shown as gasification 102, produces one or more byproducts 148. The one or more by products 148 are also provided for use in downstream operation 150.

Downstream operation 150 may involve one or more catalytic process steps in a catalytic process unit which can be a device consisting of one or more vessels and/or towers or piping arrangements, which includes the continuous stirred tank reactor (CSTR), immobilized cell reactor (ICR), trickle bed reactor (TBR), bubble column, gas lift fermenter, membrane reactor such as hollow fiber membrane bioreactor (HFMBR), static mixer, or other vessel or other device suitable for gas-liquid contact. Fixed bed, moving bed, simulated moving bed, fluidized bed, entrained bed, slurry reactor, packed bed, trickle bed, batch, semi batch, continuous, plug flow, flash, dense phase, fixed bed, downflow fixed bed, upflow expanded bed, and ebullating bed.

The types of catalysts used in the catalytic process unit can include, but are not limited to, natural clays, supported or unsupported metal or metal oxide containing catalysts, acid catalysts, zeolites, organometallic compounds. Examples include activated natural or synthetic material including activated, such as acid treated, natural clays such as bentonite type of synthesized silica-alumina or silica-magnesia, optionally with added oxides of zirconium, boron or thorium; mixed metal oxides supported on alumina or silica, such as tungsten-nickel sulfide or cobalt; metal and mixed metals containing catalysts such as platinum, palladium, rhenium, rhodium, copper, nickel, optionally supported on a silica or silica-alumina base; aluminum chloride, hydrogen chloride, sulfuric acid, hydrogen fluoride, phosphates, liquid phosphoric acid, phosphoric acid on kieselguhr, copper pyrophosphate pellets, phosphoric acid film on quarts, aluminosilicates, iron, vanadium, vanadium oxide on silica, nickel, silicone dioxide, carbonic anhydrase, iodine, zeolites, silver on alumina, Ziegler-Natta catalysts, organometallic compounds, iron oxide stabilized by chromium oxide, copper, copper-zinc-alumina, promoted iron where the promoters can be potassium oxide, aluminum oxide, and calcium oxide, and iron-chrome.

The products of gas fermentation can be catalytically converted, for example, by catalytic process unit. Additionally or alternatively, the products of gas fermentation can be catalytically converted, for example, by catalytically upgrading, into molecules, or one or more second products, wherein the one or more second products are integrated into existing or newly built infrastructure or feedstock and product transportation networks. Thus, in some embodiments, molecules produced via the catalysis of the products of gas fermentation processes may also be considered desirable products or further products of fermentation. For example, in a gas fermentation system that produces ethanol, that ethanol can reacted into a range of molecules, such as propane and benzene, toluene, ethylbenzene, xylene (BTEX), and these propane and BTEX molecules can be directly introduced into the feedstock or the existing product transportation networks/pipelines.

Ethanol and Derivatives

In one embodiment, ethanol or ethyl alcohol produced according to the method of the disclosure may be used in numerous product applications, including antiseptic hand rubs (WO 2014/100851), therapeutic treatments for methylene glycol and methanol poisoning (WO 2006/088491), as a pharmaceutical solvent for applications such as pain medication (WO 2011/034887) and oral hygiene products (U.S. Pat. No. 6,811,769), as well as an antimicrobial preservative (U.S. 2013/0230609), engine fuel (U.S. Pat. No. 1,128,549), rocket fuel (U.S. Pat. No. 3,020,708), plastics, fuel cells (U.S. Pat. No. 2,405,986), home fireplace fuels (U.S. Pat. No. 4,692,168), as an industrial chemical precursor (U.S. Pat. No. 3,102,875), cannabis solvent (WO 2015/073854), as a winterization extraction solvent (WO 2017/161387), as a paint masking product (WO 1992/008555), as a paint or tincture (U.S. Pat. No. 1,408,091), purification and extraction of DNA and RNA (WO 1997/010331), and as a cooling bath for various chemical reactions (U.S. Pat. No. 2,099,090). In addition to the foregoing, the ethanol generated by the disclosed method may be used in any other application for which ethanol might otherwise be applicable.

A further embodiment comprises converting the ethanol generated by the method into ethylene. This can be accomplished by way of an acid catalyzed dehydration of ethanol to give ethylene according to the following formula:

$$CH_3CH_2OH \rightarrow CH_2=CH_2+H_2O$$

The ethylene generated in this way may be used for a variety of applications on its own or can be used as a raw material for more refined chemical products. Specifically, ethylene alone may be used as an anesthetic, as part of a mixture with nitrogen to control ripening of fruit, as a fertilizer, as an element in the production of safety glass, as part of an oxy-fuel gas in metal cutting, welding and high velocity thermal spraying, and as a refrigerant.

As a raw material, ethylene can used in the manufacture of polymers such as polyethylene (PE), polyethylene terephthalate (PET) and polyvinyl chloride (PVC) as well as fibres and other organic chemicals. These products are used in a wide variety of industrial and consumer markets such as the packaging, transportation, electrical/electronic, textile and construction industries as well as consumer chemicals, coatings and adhesives.

Ethylene can be chlorinated to ethylene dichloride (EDC) and can then be cracked to make vinyl chloride monomer (VCM). Nearly all VCM is used to make polyvinyl chloride which has its main applications in the construction industry.

Other ethylene derivatives include alpha olefins which are used in Linear low-density polyethylene (LLDPE) production, detergent alcohols and plasticizer alcohols; vinyl acetate monomer (VAM) which is used in adhesives, paints, paper coatings and barrier resins; and industrial ethanol which is used as a solvent or in the manufacture of chemical intermediates such as ethyl acetate and ethyl acrylate.

Ethylene may further be used as a monomer base for the production of various polyethylene oligomers by way of coordination polymerization using metal chloride or metal oxide catalysts. The most common catalysts consist of titanium (III) chloride, the so-called Ziegler-Natta catalysts. Another common catalyst is the Phillips catalyst, prepared by depositing chromium (VI) oxide on silica.

Polyethylene oligomers so produced may be classified according to its density and branching. Further, mechanical properties depend significantly on variables such as the extent and type of branching, the crystal structure, and the molecular weight. There are several types of polyethylene which may be generated from ethylene, including, but not limited to:

Ultra-high-molecular-weight polyethylene (UHMWPE);
Ultra-low-molecular-weight polyethylene (ULMWPE or PE-WAX);
High-molecular-weight polyethylene (HMWPE);
High-density polyethylene (HDPE);
High-density cross-linked polyethylene (HDXLPE);
Cross-linked polyethylene (PEX or XLPE);
Medium-density polyethylene (MDPE);
Linear low-density polyethylene (LLDPE);
Low-density polyethylene (LDPE);
Very-low-density polyethylene (VLDPE); and
Chlorinated polyethylene (CPE).

Low density polyethylene (LDPE) and linear low-density polyethylene (LLDPE) mainly go into film applications such as food and non-food packaging, shrink and stretch film, and non-packaging uses. High density polyethylene (HDPE) is used primarily in blow molding and injection molding applications such as containers, drums, household goods, caps and pallets. HDPE can also be extruded into pipes for water, gas and irrigation, and film for refuse sacks, carrier bags and industrial lining.

According to one embodiment, the ethylene formed from the ethanol described above may be converted to ethylene oxide via direct oxidation according to the following formula:

$$C_2H_4+O_2 \rightarrow C_2H_4O$$

The ethylene oxide produced thereby is a key chemical intermediate in a number of commercially important processes including the manufacture of monoethylene glycol. Other EO derivatives include ethoxylates (for use in shampoo, kitchen cleaners, etc.), glycol ethers (solvents, fuels, etc.) and ethanolamines (surfactants, personal care products, etc.).

Monoethylene Glycol and Derivatives

According to one embodiment of the disclosure, the ethylene oxide produced as described above may be used to produce commercial quantities of monoethylene glycol by way of the formula:

$$(CH_2CH_2)O+H_2O \rightarrow HOCH_2CH_2OH$$

According to another embodiment, the claimed microorganism can be modified in order to directly produce monoethylene glycol. As described in WO 2019/126400, the disclosure of which is incorporated by reference herein, the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphoenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxy-pyruvate; an enzyme capable of converting 3-phospho-nooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycolaldehyde; and/or an enzyme capable of converting glycolaldehyde to ethylene glycol.

Monoethylene glycol produced according to either of the described methods may be used as a component of a variety of products including as a raw material to make polyester fibers for textile applications, including nonwovens, cover stock for diapers, building materials, construction materials, road-building fabrics, filters, fiberfill, felts, transportation upholstery, paper and tape reinforcement, tents, rope and cordage, sails, fish netting, seatbelts, laundry bags, synthetic artery replacements, carpets, rugs, apparel, sheets and pillowcases, towels, curtains, draperies, bed ticking, and blankets.

MEG may be used on its own as a liquid coolant, antifreeze, preservative, dehydrating agent, drilling fluid or any combination thereof. The MEG produced may also be used to produce secondary products such as polyester resins for use in insulation materials, polyester film, de-icing fluids, heat transfer fluids, automotive antifreeze and other liquid coolants, preservatives, dehydrating agents, drilling fluids, water-based adhesives, latex paints and asphalt emulsions, electrolytic capacitors, paper, and synthetic leather.

Importantly, the monoethylene glycol produced may be converted to the polyester resin polyethylene terephthalate ("PET") according to one of two major processes. The first process comprises transesterification of the monoethylene glycol utilizing dimethyl terephthalate, according to the following two-step process:

First Step

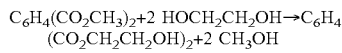

$$C_6H_4(CO_2CH_3)_2 + 2\ HOCH_2CH_2OH \rightarrow C_6H_4(CO_2CH_2CH_2OH)_2 + 2\ CH_3OH$$

Second Step

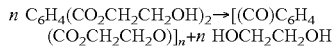

$$n\ C_6H_4(CO_2CH_2CH_2OH)_2 \rightarrow [(CO)C_6H_4(CO_2CH_2CH_2O)]_n + n\ HOCH_2CH_2OH$$

Alternatively, the monoethylene glycol can be the subject of an esterification reaction utilizing terephthalic acid according to the following reaction:

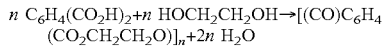

$$n\ C_6H_4(CO_2H)_2 + n\ HOCH_2CH_2OH \rightarrow [(CO)C_6H_4(CO_2CH_2CH_2O)]_n + 2n\ H_2O$$

The polyethylene terephthalate produced according to either the transesterification or esterification of monoethylene glycol has significant applicability to numerous packaging applications such as jars and, in particular, in the production of bottles, including plastic bottles. It can also be used in the production of high-strength textile fibers such as Dacron, as part of durable-press blends with other fibers such as rayon, wool, and cotton, for fiber fillings used in insulated clothing, furniture, and pillows, in artificial silk, as carpet fiber, automobile tire yarns, conveyor belts and drive belts, reinforcement for fire and garden hoses, seat belts, nonwoven fabrics for stabilizing drainage ditches, culverts, and railroad beds, and nonwovens for use as diaper topsheets, and disposable medical garments.

At a higher molecular weight, PET can be made into a high-strength plastic that can be shaped by all the common methods employed with other thermoplastics. Magnetic recording tape and photographic film are produced by extrusion of PET film. Molten PET can be blow-molded into transparent containers of high strength and rigidity that are also virtually impermeable to gas and liquid. In this form, PET has become widely used in bottles, especially plastic bottles, and in jars.

Isopropanol and Derivatives

In an additional embodiment, isopropanol or isopropyl alcohol (IPA) produced according to the method may be used in numerous product applications, including either in isolation or as a feedstock for the production for more complex products. Isopropanol may also be used in solvents for cosmetics and personal care products, de-icers, paints and resins, food, inks, adhesives, and pharmaceuticals, including products such as medicinal tablets as well as disinfectants, sterilizers, and skin creams.

The IPA produced may be used in the extraction and purification of natural products such as vegetable and animal oil and fats. Other applications include its use as a cleaning and drying agent in the manufacture of electronic parts and metals, and as an aerosol solvent in medical and veterinary products. It can also be used as a coolant in beer manufacture, a coupling agent, a polymerization modifier, a de-icing agent and a preservative.

Alternatively, the IPA produced according to the method of the disclosure may be used to manufacture additional useful compounds, including plastics, derivative ketones such as methyl isobutyl ketone (MIBK), isopropylamines and isopropyl esters. Still further, the IPA may be converted to propylene according to the following formula:

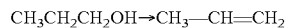

$$CH_3CH_2CH_2OH \rightarrow CH_3-CH=CH_2$$

The propylene produced may be used as a monomer base for the production of various polypropylene oligomers by way of chain-growth polymerization via either gas-phase or bulk reactor systems. The most common catalysts consist of titanium (III) chloride, the so-called Ziegler-Natta catalysts and metallocene catalysts.

Polypropylene oligomers so produced may be classified according to tacticity and can be formed into numerous products by either extrusion or molding of polypropylene pellets, including piping products, heat-resistant articles such as kettles and food containers, disposable bottles (including plastic bottles), clear bags, flooring such as rugs and mats, ropes, adhesive stickers, as well as foam polypropylene which can be used in building materials. Polypropylene may also be used for hydrophilic clothing and medical dressings.

Commodity Chemicals and Articles

According to one embodiment, the gas fermentation product is a commodity chemical. In another embodiment, the gas fermentation product is a commodity chemical, where the commodity chemical is catalytically converted, for example, by catalytically upgrading, into molecules, or one or more second products, wherein the one or more second products are integrated into existing or newly built infrastructure or feedstock and product transportation networks. In one embodiment, wherein the commodity chemical is selected from ethanol, isopropanol, monoethylene glycol, sulfuric acid, propylene, sodium hydroxide, sodium carbonate, ammonia, benzene, acetic acid, ethylene, ethylene oxide, formaldehyde, methanol, or any combination thereof.

In one embodiment, the commodity chemical is aluminum sulfate, ammonia, ammonium nitrate, ammonium sulfate, carbon black, chlorine, diammonium phosphate, monoammonium phosphate, hydrochloric acid, hydrogen fluoride, hydrogen peroxide, nitric acid, oxygen, phosphoric acid, sodium silicate, titanium dioxide, or any combination thereof. In another embodiment, the commodity chemical is acetic acid, acetone, acrylic acid, acrylonitrile, adipic acid, benzene, butadiene, butanol, caprolactam, cumene, cyclohexane, dioctyl phthalate, ethylene glycol, methanol, octanol, phenol, phthalic anhydride, polypropylene, polystyrene, polyvinyl chloride, polypropylene glycol, propylene oxide, styrene, terephthalic acid, toluene, toluene diisocyanate, urea, vinyl chloride, xylenes, or any combination thereof.

Feedstock Preparation Byproducts

The disclosed systems and methods are also suitable for providing one or more feedstock preparation byproducts, referred to as secondary products, that are independent of the gas fermentation product (e.g., ethylene, ethanol, acetate, etc.). For example, in certain embodiments, microbial biomass itself may be considered a secondary product. In such embodiments, biomass from a bioreactor, such as dead microorganisms, may be used as a carbon source for further fermentation by gasifying the biomass. Additionally or alternatively, microbial proteins or other biomass may be recovered from a bioreactor and sold/used separately from the primary product (e.g., ethylene, ethanol, acetate, 1-butanol, etc.) as a supplement, such as a nutritional supplement and/or an animal feed. Known methods for using such biomass as a nutritional supplement or animal feed are disclosed in U.S. Pat. No. 10,856,560, which is herein incorporated by reference.

Additionally or alternatively, char may be a secondary product. In embodiments that involve or comprise gasification of solid or liquid carbonaceous materials to produce a feedstock, char can be incidentally produced. Char is carbon rich and highly structured, and therefore it can be useful as, for example, fertilizer. However, as disclosed herein the char is advantageously provided to a downstream operation for the production of an article of manufacture. A particular example is the incorporation of the char produced in the gasification being supplied to a downstream operation for the production of tires. For example, char may be incorporated as an ingredient into the production of new tires. Both the fermentation product and the char may be provided to the same downstream operation to produce an article of manufacture, to the same or different steps within the operation. The downstream operation may be to produce rubber containing articles, such as, for example, tires. The char may be further processed being provided to the downstream operation. For example the char may be processed to form carbon black which is then provided to the downstream operation. This embodiment is particularly valuable when the downstream operation is an operation to produce a rubber containing article such as tires.

Another byproduct or secondary of the feedstock preparation may be silica containing sludge. Such sludge may be produced in gasification with particular types of gasifiers. The silica may be recovered from the sludge and provided to a downstream operation to produce an article of manufacture. Both the fermentation product and the recovered silica may be provided to the same downstream operation to produce an article of manufacture, to the same or different steps within the operation. The downstream operation may be to produce rubber containing articles, such as, for example, tires.

Yet another byproduct or secondary of the feedstock preparation may be a metal or metal oxide. Such metal or metal oxide may be produced in gasification with particular types of gasifiers. The metal or metal oxide may be recovered from the gasifier and provided to a downstream operation to produce an article of manufacture. Both the fermentation product and the recovered silica may be provided to the same downstream operation to produce an article of manufacture, to the same or different steps within the operation. The downstream operation may be to produce rubber containing articles, such as, for example, tires. When the downstream operation is to produce tires, the metal may be zinc and the metal oxide maybe zinc oxide. Since zinc and or zinc oxide is particularly apt to be present when the at least one material gasified in the gasifier is a tire or portions of tires, it is most advantageous when the downstream operation is to produce new tires.

Yet another byproduct or secondary of the feedstock preparation may be a steel. Such steel may be recovered from gasification with particular types of pretreatment techniques such as, for example, pyrolysis. The steel may be recovered from the pretreatment unit and provided to a downstream operation to produce an article of manufacture. Both the fermentation product and the recovered steel may be provided to the same downstream operation to produce an article of manufacture, to the same or different steps within the operation. The downstream operation may be to produce rubber containing articles, such as, for example, tires. When the downstream operation is to produce tires, the steel is particularly valuable. Since steel is particularly apt to be present when the at least one material processed in the feedstock pretreatment, such as pyrolysis, is a whole tire or portions of a tire with the steel components not removed, it is most advantageous when the downstream operation is to produce new tires.

One or more byproducts of the feedstock preparation may be produced and recovered. One or more of the byproducts produced and recovered may be provided to the downstream operation. Two or more byproducts of the feedstock preparation may be produced and recovered and provided to the same downstream operation. The two or more byproducts may be provided to the same or different steps of the downstream operation. Three or more byproducts of the feedstock preparation may be produced and recovered and provided to the same downstream operation. The three or more byproducts may be provided to the same or different steps of the downstream operation. Four or more byproducts of the feedstock preparation may be produced and recovered and provided to the same downstream operation. The four or more byproducts may be provided to the same or different steps of the downstream operation. The byproducts of the feedstock preparation may be produced and recovered and provided to the same downstream operation to which the gas fermentation product is provided.

Additionally or alternatively, unutilized carbon dioxide, which may be in the form of an off-gas from the gas fermentation, may be a secondary product used within the gas fermentation process. Such unutilized carbon dioxide will be in a stoichiometrically higher proportion in the off-gas compared to the feedstock, and this relative purity can make the carbon dioxide useful. For example, the unutilized carbon can be sequestered by an operator for the purposes of obtaining carbon credits, or it may be combined with hydrogen gas ($H_2$), such as "green hydrogen" resulting from electrolysis, and recycled back into the gas fermenter or bioreactor as feedstock.

B. Microorganisms and Fermentation

The disclosed systems and methods integrate microbial fermentation into existing or newly built infrastructure of, for example, a gas (e.g., natural gas) transportation pipeline, oil well, or the like to convert various feedstocks, gas, or other by-products into useful products such as ethylene. As disclosed herein, the systems allow for feedstocks, gas, or other by-products to be directly provided to a bioreactor, and the bioreactor is directly connected to a system for facilitating transport of a desirable product of fermentation to an end point (e.g., a chemical plant or refinery). In particular, the disclosed systems and methods are applicable for producing useful products (e.g., ethylene, ethanol, acetate, etc.) from gaseous substrates, such as gases that may optionally contain $H_2$, that are utilized as a carbon source by microbial cultures. Such microorganisms may include bacteria, archaea, algae, or fungi (e.g., yeast), and these classes of microorganism may be suitable for the disclosed systems and methods. In general, the selection of the microorganism(s) is not particularly limited so long as the microorganism is C1-fixing, carboxydotrophic, acetogenic, methanogenic, capable of Wood-Ljungdahl synthesis, a hydrogen oxidizer, autotrophic, chemolithoautotrophic, or any combination thereof. Among the various suitable classes of microorganisms, bacteria are particularly well suited for integration in the disclosed systems and methods.

When bacteria are utilized in the disclosed systems and methods, the bacteria may be aerobic or anaerobic, depending on the nature of the carbon source and other inputs being fed into the bioreactor or fermentation unit. Further, the bacteria utilized in the disclosed systems and methods can include one or more strains of carboxydotrophic bacteria. In particular embodiments, the carboxydotrophic bacterium can be selected from a genus including, but not limited to, *Cupriavidus, Clostridium, Moorella, Carboxydothermus, Ruminococcus, Acetobacterium, Eubacterium, Butyribacterium, Oxobacter, Methanosarcina, Methanosarcina,* and *Desulfotomaculum*. In particular embodiments, the carboxydotrophic bacterium is *Clostridium autoethanogenum*. In other particular embodiments, the carboxydotrophic bacterium is *Cupriavidus necator*.

A number of anaerobic bacteria are known to be capable of carrying out fermentation for the disclosed methods and system. Examples of such bacteria that are suitable for use in the invention include bacteria of the genus *Clostridium*, such as strains of *Clostridium ljungdahlii* (including those described in WO 00/68407, EP 117309, U.S. Pat. Nos. 5,173,429, 5,593,886, and 6,368,819, WO 98/00558 and WO 02/08438), *Clostridium carboxydivorans* (Liou et al., International Journal of Systematic and Evolutionary Microbiology 33: pp. 2,085-2091) and *Clostridium autoethanogenum* (Abrini et al., Archives of Microbiology 161: pp 345-351). Other suitable bacteria include those of the genus *Moorella*, including *Moorella* sp HUC22-1 (Sakai et al., Biotechnology Letters 29: pp. 1,607-1612), and those of the genus *Carboxydothermus* (Svetlichny, V. A., et al. (1991), Systematic and Applied Microbiology 14:254-260). The disclosures of each of these publications are incorporated herein by reference. In addition, other carboxydotrophic anaerobic bacteria can be used in the disclosed systems and methods by a person of skill in the art. It will also be appreciated upon consideration of the instant disclosure that a mixed culture of two or more bacteria may be used in the disclosed systems and methods. All of the foregoing patents, patent applications, and non-patent literature are incorporated herein by reference in their entirety.

One exemplary anaerobic bacteria that is suitable for use in the disclosed systems and methods is *Clostridium autoethanogenum*. In some embodiments, the *Clostridium autoethanogenum* is a *Clostridium autoethanogenum* having the identifying characteristics of the strain deposited at the German Resource Centre for Biological Material (DSMZ) under the identifying deposit number 19630. In some embodiments, the *Clostridium autoethanogenum* is a *Clostridium autoethanogenum* having the identifying characteristics of DSMZ deposit number DSMZ 10061. In some embodiments, the *Clostridium autoethanogenum* is a *Clostridium autoethanogenum* having the identifying characteristics of DSMZ deposit number DSMZ 23693.

In some embodiments, the anaerobic bacteria is *Clostridium carboxidivorans* having the identifying characteristics of deposit number DSM15243. In some embodiments, the anaerobic bacteria is *Clostridium drakei* having the identifying characteristics of deposit number DSM12750. In some embodiments, the anaerobic bacteria is *Clostridium ljungdahlii* having the identifying characteristics of deposit number DSM13528. Other suitable *Clostridium ljungdahlii* strains may include those described in WO 00/68407, EP 117309, U.S. Pat. Nos. 5,173,429, 5,593,886, and 6,368,819, WO 98/00558 and WO 02/08438, all of which are incorporated herein by reference. In some embodiments, the anaerobic bacteria is *Clostridium scatologenes* having the identifying characteristics of deposit number DSM757. In some embodiments, the anaerobic bacteria is *Clostridium ragsdalei* having the identifying characteristics of deposit number ATCC BAA-622.

In some embodiments, the anaerobic bacteria is *Acetobacterium woodii*. In some embodiments, the anaerobic bacteria is from the genus *Moorella*, such as *Moorella* sp HUC22-1, (Sakai et al, Biotechnology Letters, 29: pp. 1,607-1612). Further examples of suitable anaerobic bacteria include, but are not limited to, *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other C1-fixing, carboxydotrophic anaerobes may be suitable for the disclosed systems and methods. It will also be appreciated that a mixed culture of two or more bacteria may be utilized as well.

A number of aerobic bacteria are known to be capable of carrying out fermentation for the disclosed methods and system. Examples of such bacteria that are suitable for use in the invention include bacteria of the genus *Cupriavidus* and *Ralstonia*. In some embodiments, the aerobic bacteria is *Cupriavidus necator* or *Ralstonia eutropha*. In some embodiments, the aerobic bacteria is *Cupriavidus alkaliphilus*. In some embodiments, the aerobic bacteria is *Cupriavidus basilensis*. In some embodiments, the aerobic bacteria is *Cupriavidus campinensis*. In some embodiments, the aerobic bacteria is *Cupriavidus gilardii*. In some embodiments, the aerobic bacteria is *Cupriavidus laharis*. In some embodiments, the aerobic bacteria is *Cupriavidus metallidurans*. In some embodiments, the aerobic bacteria is *Cupriavidus nantongensis*. In some embodiments, the aerobic bacteria is *Cupriavidus numazuensis*. In some embodiments, the aerobic bacteria is *Cupriavidus oxalaticus*. In some embodiments, the aerobic bacteria is *Cupriavidus pampae*. In some embodiments, the aerobic bacteria is *Cupriavidus pauculus*. In some embodiments, the aerobic bacteria is *Cupriavidus pinatubonensis*. In some embodiments, the aerobic bacteria is *Cupriavidus plantarum*. In some embodiments, the aerobic bacteria is *Cupriavidus respiraculi*. In some embodiments, the aerobic bacteria is *Cupriavidus taiwanensis*. In some embodiments, the aerobic bacteria is *Cupriavidus yeoncheonensis*.

The fermentation may be carried out in any suitable bioreactor. In some embodiments, the bioreactor may comprise a first, growth reactor in which the microorganisms (e.g., bacteria) are cultured, and a second, fermentation reactor, to which fermentation broth from the growth reactor is fed and in which most of the fermentation product (e.g. ethylene, ethanol, acetate, etc.) is produced.

It will be appreciated that for growth of the bacteria and fermentation to occur, in addition to a carbon-containing substrate gas, a suitable liquid nutrient medium will need to be fed to the bioreactor. A nutrient medium will contain vitamins and minerals sufficient to permit growth of the micro-organism used. Aerobic and anaerobic media suitable for the fermentation using carbon-containing substrate gases as the sole carbon source are known in the art. For example, suitable media are described in U.S. Pat. Nos. 5,173,429 and 5,593,886 and WO 02/08438, WO2007/115157 and WO2008/115080, referred to above and all of which are incorporated herein by reference. Further, the fermentation can be carried out under appropriate conditions for the desired fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations, and maximum product concentrations to avoid product inhibition.

The optimum reaction conditions will depend partly on the particular micro-organism used. However, in general, it may be preferable that the fermentation be performed at a pressure higher than ambient pressure. Operating at increased pressures may allow for, for example, a significant increase in the rate of CO transfer from the gas phase to the liquid phase where it can be taken up by the micro-organism as a carbon source. This, in turn, means that the retention time (defined as the liquid volume in the bioreactor divided by the input gas flow rate) can be reduced when bioreactors are maintained at elevated pressure rather than atmospheric pressure. Also, since a given CO, or $CO_2$ and $H_2$ conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment.

Similarly, temperature of the culture may vary as needed. For example, in some embodiments, the fermentation is carried out at a temperature of about 34° C. to about 37° C. In some embodiments, the fermentation is carried out at a temperature of about 34° C. This temperature range may assist in supporting or increasing the efficiency of fermentation including, for example, maintaining or increasing the growth rate of bacteria, extending the period of growth of bacteria, maintaining or increasing production of the desired product (e.g., ethylene, ethanol, acetate, etc.), or maintaining or increasing CO or $CO_2$ uptake or consumption.

Culturing of the bacteria used in the disclosed systems and methods may be conducted using any number of processes known in the art for culturing and fermenting substrates. In some embodiments a culture of a bacterium can be maintained in an aqueous culture medium. For example, the aqueous culture medium may be a minimal anaerobic microbial growth medium. Suitable media are known in the art and described for example in U.S. Pat. Nos. 5,173,429 and 5,593,886; WO 02/08438, and in Klasson et al (1992), Bioconversion of Synthesis Gas into Liquid or Gaseous Fuels, *Enz. Microb. Technol.* 14:602-608; Najafpour and Younesi (2006) Ethanol and acetate synthesis from waste gas using batch culture of *Clostridium ljungdahlii*. *Enzyme and Microbial Technology*, 38(1-2):223-228; and Lewis et al (2002), Making the connection-conversion of biomass-generated producer gas to ethanol, *Abst. Bioenergy, p.* 2091-2094.

Further general processes for using gaseous substrates for fermentation that may be utilized for the disclosed systems and methods are described in the following disclosures: WO98/00558, M. Demler and D. Weuster-Botz (2010), Reaction Engineering Analysis of Hydrogenotrophic Production of Acetic Acid by *Acetobacterium woodii*, *Biotechnology and Bioengineering*; D. R. Martin, A. Misra and H. L. Drake (1985), Dissimilation of Carbon Monoxide to Acetic Acid by Glucose-Limited Cultures of *Clostridium thermoaceticum*, *Applied and Environmental Microbiology*, 49(6):1412-1417. Further processes generally described in the following articles using gaseous substrates for fermentation may also be utilized: (i) K. T. Klasson, et al. (1991), Bioreactors for synthesis gas fermentations resources, *Conservation and Recycling*, 5:145-165; (ii) K. T. Klasson, et al. (1991), Bioreactor design for synthesis gas fermentations, *Fuel*, 70:605-614; (iii) K. T. Klasson, et al. (1992), Bioconversion of synthesis gas into liquid or gaseous fuels, *Enzyme and Microbial Technology*, 14:602-608; (iv) J. L. Vega, et al. (1989), Study of Gaseous Substrate Fermentation: Carbon Monoxide Conversion to Acetate. 2. Continuous Culture, *Biotech. Bioeng.*, 34(6):785-793; (vi) J. L. Vega, et al. (1989), Study of gaseous substrate fermentations: Carbon monoxide conversion to acetate. 1. Batch culture, *Biotech. Bioeng.*, 34 (6): 774-784; (vii) J. L. Vega, et al. (1990), Design of Bioreactors for Coal Synthesis Gas Fermentations, *Resources, Conservation and Recycling*, 3:149-160; all of which are incorporated herein by reference.

As noted above, while bacteria may be preferred microorganisms for the disclosed systems and methods, other microorganisms like yeast may also be suitable. For example, yeast that may be used in the disclosed systems and methods include genus *Cryptococcus*, such as strains of *Cryptococcus curvatus* (also known as *Candida curvatus*) (see Chi et al. (2011), Oleaginous yeast *Cryptococcus curvatus* culture with dark fermentation hydrogen production effluent as feedstock for microbial lipid production, *International Journal of Hydrogen Energy*, 36:9542-9550, which is incorporated herein by reference). Other suitable yeasts include those of the genera *Candida, Lipomyces, Rhodosporidium, Rhodotorula, Saccharomyces*, and *Yarrowia*. In addition, it should be understood that the disclosed systems and methods may utilize a mixed culture of two or more yeasts. Additional fungi that may be suitable for the disclosed systems and methods include, but are not limited to, fungi selected from *Blakeslea, Cryptococcus, Cunninghamella, Mortierella, Mucor, Phycomyces, Pythium, Thraustochytrium* and *Trichosporon*. Culturing of yeast or other fungi may be conducted using any number of processes known in the art for culturing and fermenting substrates using yeasts or fungi.

Typically, fermentation is carried out in any suitable bioreactor, such as a continuous stirred tank reactor (CTSR), a bubble column reactor (BCR) or a trickle bed reactor (TBR). Also, in some embodiments, the bioreactor may comprise a first, growth reactor in which the micro-organisms are cultured, and a second, fermentation reactor, to which fermentation broth from the growth reactor is fed and in which most of the fermentation product (e.g., ethylene, ethanol, acetate, etc.) is produced.

The disclosed systems and method may comprise a primary bioreactor and a secondary bioreactor. The efficiency of the fermentation processes may be further improved by a further process of recycling a stream exiting the secondary bioreactor to at least one primary reactor. The stream exiting the secondary bioreactor may contain unused substrates, salts, and other nutrient components. By recycling the exit stream to a primary reactor, the cost of providing a continuous nutrient media to the primary reactor can be reduced. This recycling step has the further benefit of potentially reducing the water requirements of the continuous fermentation process. The stream exiting the bioreactor can optionally be treated before being passed back to a primary reactor. For example, because yeasts generally require oxygen for growth, any media recycled from a secondary bioreactor to a primary bioreactor may need to have all oxygen substantially removed, as any oxygen present in the primary bioreactor will be harmful to an anaerobic culture in the primary bioreactor. Therefore, the broth stream exiting the secondary bioreactor may be passed through an oxygen scrubber to remove substantially all of the oxygen prior to being passed to the primary reactor. In some embodiments, biomass from a bioreactor (e.g., a primary bioreactor, secondary bioreactor, or any combination thereof) may be separated and processed to recover one or more products.

In some embodiments, both anaerobic and aerobic gases can be used to feed separate cultures (e.g., an anaerobic culture and an aerobic culture) in two or more different bioreactors that are both integrated into the same process stream.

As disclosed herein, the feedstock gas stream providing a carbon source for the disclosed cultures is not particularly limited, so long as it contains a carbon source. C1 feedstocks comprising methane, carbon monoxide, carbon dioxide, or any combination thereof may be preferred. Optionally, $H_2$ may also be present in the feedstock. In some embodiments, the feedstock may comprise a gaseous substrates comprising substrate comprising carbon monoxide. In some embodiments, the feedstock may comprise a gaseous substrates comprising substrate comprising carbon dioxide. In some embodiments, the feedstock may comprise a gaseous substrates comprising substrate comprising both carbon monoxide and carbon dioxide. In some embodiments, the feedstock may comprise a gaseous substrates comprising carbon monoxide. In some embodiments, the feedstock may comprise a gaseous substrates comprising carbon dioxide. In some embodiments, the feedstock may comprise a gaseous substrates comprising carbon monoxide, carbon dioxide, or any combination thereof.

Regardless of the source or precise content of the gas used as a feedstock, the feedstock may be metered (e.g., for carbon credit calculations or mass balancing of sustainable carbon with overall products) into a bioreactor in order to maintain control of the follow rate and amount of carbon provided to the culture. Similarly, the output of the bioreactor may be metered (e.g., for carbon credit calculations or mass balancing of sustainable carbon with overall products) or comprise a valved connection that can control the flow of the output and products (e.g., ethylene, ethanol, acetate, 1-butanol, etc.) produced via fermentation. Such a valve or metering mechanism can be useful for a variety of purposes including, but not limited to, slugging of product through a connected pipeline and measuring the amount of output from a given bioreactor such that if the product is mixed with other gases or liquids the resulting mixture can later be mass balanced to determine the percentage of the product that was produced from the bioreactor.

The microorganisms of the disclosure may be cultured with the gaseous substrate to produce one or more products. For instance, the microorganism may produce or may be engineered to produce ethanol (WO 2007/117157, U.S. Pat. No. 7,972,824), acetate (WO 2007/117157, U.S. Pat. No. 7,972,824), 1-butanol (WO 2008/115080, U.S. Pat. No. 8,293,509, WO 2012/053905, U.S. Pat. No. 9,359,611 and WO 2017/066498, U.S. Pat. No. 9,738,875), butyrate (WO 2008/115080, U.S. Pat. No. 8,293,509), 2,3-butanediol (WO 2009/151342, U.S. Pat. No. 8,658,408 and WO 2016/094334, U.S. Pat. No. 10,590,406), lactate (WO 2011/112103, U.S. Pat. No. 8,900,836), butene (WO 2012/024522, US2012/045807), butadiene (WO 2012/024522, US 2012/045807), methyl ethyl ketone (2-butanone) (WO 2012/024522, US 2012/045807 and WO 2013/185123, U.S. Pat. No. 9,890,384), ethanol which is then converted to ethylene (WO 2012/026833, US 2013/157,322), acetone (WO 2012/115527, U.S. Pat. No. 9,410,130), isopropanol (WO 2012/115527 U.S. Pat. No. 9,410,130), lipids (WO 2013/036147 U.S. Pat. No. 9,068,202), 3-hydroxypropionate (3-HP) (WO 2013/180581, U.S. Pat. No. 9,994,878), terpenes, including isoprene (WO 2013/180584, U.S. Pat. No. 10,913,958), fatty acids (WO 2013/191567 U.S. Pat. No. 9,347,076), 2-butanol (WO 2013/185123 U.S. Pat. No. 9,890,384), 1,2-propanediol (WO 2014/036152, U.S. Pat. No. 9,284,564), 1-propanol (WO 2014/0369152, U.S. Pat. No. 9,284,564), 1 hexanol (WO 2017/066498, U.S. Pat. No. 9,738,875), 1 octanol (WO 2017/066498, U.S. Pat. No. 9,738,875), chorismate-derived products (WO 2016/191625, U.S. Pat. No. 10,174,303), 3-hydroxybutyrate (WO 2017/066498, U.S. Pat. No. 9,738,875), 1,3-butanediol (WO 2017/066498, U.S. Pat. No. 9,738,875), 2-hydroxyisobutyrate or 2-hydroxyisobutyric acid (WO 2017/066498, U.S. Pat. No. 9,738,875), isobutylene (WO 2017/066498, U.S. Pat. No. 9,738,875), adipic acid (WO 2017/066498, U.S. Pat. No. 9,738,875), 1,3-hexanediol (WO 2017/066498, U.S. Pat. No. 9,738,875), 3-methyl-2-butanol (WO 2017/066498, U.S. Pat. No. 9,738,875), 2-buten-1-ol (WO 2017/066498, U.S. Pat. No. 9,738,875), isovalerate (WO 2017/066498, U.S. Pat. No. 9,738,875), isoamyl alcohol (WO 2017/066498, U.S. Pat. No. 9,738,875), and/or monoethylene glycol (WO 2019/126400, U.S. Pat. No. 11,555,209) in addition to 2-phenylethanol (WO 2021/188190, US 2021/0292732) and ethylene.

Substrates and C1-Carbon Sources

A portion of the substrate and/or C1-carbon source may be a gas obtained as a by-product of an industrial process or from another source, such as combustion engine exhaust fumes, biogas, landfill gas, direct air capture, flaring, or from electrolysis. However, a portion of the substrate and/or C1-carbon source is syngas generated by pyrolysis, torrefaction, reforming, or gasification. In other words, carbon in solid or liquid materials may be recycled by pyrolysis, torrefaction, reforming, or gasification to generate syngas which is used as the substrate and/or C1-carbon source in gas fermentation. A portion of the substrate and/or C1-carbon source may be natural gas, carbon dioxide from conventional and unconventional gas production, and or a gas comprising methane. Gas fermentation processes are flexible and any of these substrate and/or C1-carbon sources may be employed.

In certain embodiments, the industrial process source of an optional portion of the substrate and/or C1 carbon source is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anaerobic digestion, catalytic processes, natural gas extraction, cellulosic fermentation, oil extraction, industrial processing of geological reservoirs, processing fossil resources such as natural gas coal and oil, landfill operations, or any combination thereof. Examples of specific processing steps within an industrial process include catalyst regeneration, fluid catalyst cracking, and catalyst regeneration. Air separation and direct air capture are other suitable industrial processes. Specific examples in steel and ferroalloy manufacturing include blast furnace gas, basic oxygen furnace gas, coke oven gas, direct reduction of iron furnace top-gas, and residual gas from smelting iron. Other general examples include flue gas from fired boilers and fired heaters, such as natural gas, oil, or coal fired boilers or heaters, and gas turbine exhaust. Another example is the flaring of compounds such as at oil and gas production sites. In these embodiments, the substrate and/or C1-carbon source may be captured from the industrial process before it is emitted into the atmosphere, using any known method.

The substrate and/or C1-carbon source is synthesis gas known as syngas, which may be obtained from reforming, partial oxidation, plasma, or gasification processes. Examples of gasification processes include gasification of coal, gasification of refinery residues, gasification of petroleum coke, gasification of biomass, gasification of lignocellulosic material, gasification of wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of landfill gas, gasification of biogas such as when biogas is added to enhance gasification of another material, gasification of rubber containing material, including portions of tires and whole tires. Examples of reforming processes include, steam methane reforming, steam naphtha reforming, reforming of natural gas, reforming of biogas, reforming of landfill gas, reforming of coke oven gas, reforming of pyrolysis off-gas, reforming of ethylene production off-gas, naphtha reforming, and dry methane reforming. Examples of partial oxidation processes include thermal and catalytic partial oxidation processes, catalytic partial oxidation of natural gas, partial oxidation of hydrocarbons, partial oxidation of biogas, partial oxidation of landfill gas, or partial oxidation of pyrolysis off-gas. Examples of municipal solid waste include tires, plastics, refuse derived fuel, and fibers such as in shoes, apparel, and textiles. Municipal solid waste may be simply landfill-type waste and may be sorted or unsorted. Examples of biomass may include lignocellulosic material and microbial biomass. Lignocellulosic material may include agriculture by-products, forest by-products, and some industrial by-products. Whole tires may be processed by pyrolysis to form syngas.

Biomass may be created as by-products of "nature-based solutions" (NBS) and thus natured-based solutions may provide feedstock to the gas fermentation process. Nature-based solutions is articulated by the European Commission as solutions inspired and supported by nature, which are cost-effective, simultaneously provide environmental, social, and economic benefits and help build resilience. Such solutions bring more, and more diverse, nature and natural features and processes into cities, landscapes, and seascapes, through locally adapted, resource-efficient, and systemic interventions. Nature-based solutions must benefit biodiversity and support the delivery of a range of ecosystem services. Through the use of NBS healthy, resilient, and diverse ecosystems (whether natural, managed, or newly created) can provide solutions for the benefit of both societies and overall biodiversity. Examples of nature-based solutions include natural climate solutions (conservation, restoration and improved land management that increase carbon storage or avoid greenhouse gas emissions in landscapes and wetlands across the globe), halting biodiversity loss, socio-economic impact efforts, habitat restoration, and health and wellness efforts with respect to air and water. Biomass produced through nature-based solutions may be used as feedstock to gas fermentation processes.

A portion of the substrate and/or C1-carbon source may be a gas stream comprising methane. Such a methane containing gas may be obtained from: fossil methane emissions such as during fracking, wastewater treatment, livestock, agriculture, and municipal solid waste landfills. It is also envisioned that the methane may be burned to produce electricity or heat and the C1 by-products may be used as the substrate or carbon source. The substrate and/or C1-carbon source may be a gas stream comprising natural gas.

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology.

All patents, patent applications, and published references cited herein are hereby incorporated by reference in their entirety. The claims are intended to cover the components and steps in any sequence which is effective to meet the objectives there intended unless the context specifically indicates the contrary.

The use of the terms "a" and "an" and "the" and similar terms are to be construed to cover both the singular and the plural, unless otherwise indicated herein or clearly contradicted by context. The terms "comprising," "having," "including," and "containing" are to be construed as open-ended terms unless otherwise noted. The use of the alternative, such as the term "or", should be understood to mean either one, both, or any combination thereof of the alternatives.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention, and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EMBODIMENTS OF THE DISCLOSURE

Embodiment 1. An integrated process comprising:
  a. processing at least one material comprising carbon atoms, in a partial oxidation, pyrolysis, torrefaction, reforming, or gasification process, to produce a raw syngas steam comprising at least carbon monoxide and carbon dioxide, and to produce at least one byproduct selected from a metal, metal oxide, silica, steel, or char;
  b. passing at least a portion of the syngas stream to a gas fermentation process comprising a bioreactor containing a C1-fixing microorganism in a liquid nutrient medium to produce at least one fermentation product; and
  c. providing the at least one byproduct and the at least one fermentation product to a downstream operation to produce an article of manufacture.
Embodiment 2. The process of embodiment 1 wherein at least two byproducts are produced by the partial oxidation, pyrolysis, torrefaction, reforming, or gasification process and both byproducts are provided to the downstream operation to produce an article of manufacture.
Embodiment 3. The process of embodiment 1 or 2 wherein at least three byproducts are produced by the partial oxidation, pyrolysis, torrefaction, reforming, or gasification process and all three byproducts are provided for use in the downstream operation to produce an article of manufacture.
Embodiment 4. The process of any of embodiments 1 to 3 wherein at least four byproducts are produced by the partial oxidation, pyrolysis, torrefaction, reforming, or gasification process and all four byproducts are provided for use in the downstream operation to produce an article of manufacture.
Embodiment 5. The process of any of embodiments 1 to 4 wherein the metal or metal oxide comprises zinc.
Embodiment 6. The process of any of embodiments 1 to 5 further comprising processing the char to generate carbon black prior to being provided for use in the downstream operation to produce an article of manufacture.
Embodiment 7. The process of any of embodiments 1 to 6 wherein the at least one material comprises a whole tire or at least a portion of a tire.
Embodiment 8. The process of any of embodiments 1 to 7 wherein the tire is an end of life tire.
Embodiment 9. The process of any of embodiments 1 to 8 wherein the downstream operation to produce an article of manufacture is at least one step of a tire production process.
Embodiment 10. The process of any of embodiments 1 to 8 wherein two or more byproducts are produced by the partial oxidation, pyrolysis, torrefaction, reforming, or gasification process and the two or more byproducts are provided to the same or different steps of a production process to manufacture a tire.
Embodiment 11. The process of any of embodiments 1 to 10 wherein the at least one material comprises a natural or synthetic rubber containing material.
Embodiment 12. The process of any of embodiments 1 to 11 wherein the downstream operation to produce an article of manufacture is at least one step of a production process to manufacture a rubber containing article.
Embodiment 13. The process of any of embodiment 1 to 12 wherein two or more byproducts are produced by the partial oxidation, pyrolysis, torrefaction, reforming, or gasification process and the two or more byproducts are provided to the same or different steps of the production process to manufacture a rubber containing article.
Embodiment 14. The process of any of embodiments 1 to 13 wherein the fermentation product is selected from selected from an alcohol, an acid, a diacid, an alkene, a terpene, an isoprene, and alkyne.
Embodiment 15. The process of any of embodiments 1 to 14 wherein the C1-fixing microorganism is an acetogenic carboxydotrophic microorganism.
Embodiment 16. The process of any of embodiments 1 to 15 wherein microorganism is selected from a genus of *Clostridium, Moorella, Carboxydothermus, Ruminococcus, Acetobacterium, Eubacterium, Butyribacterium, Oxobacter, Methanosarcina, Methanosarcina, Desulfotomaculum*, or *Cupriavidus*.
Embodiment 17. The process of any of embodiments 1 to 16 wherein the gas fermentation product and the at least one byproduct are provided to the same or different steps of the downstream operation to produce an article of manufacture.
Embodiment 18. The process of any of embodiments 1 to 17 wherein the at least one material is selected from coal, refinery residues, petroleum coke, biomass, lignocellulosic material, black liquor, municipal solid waste, municipal liquid waste, industrial solid waste, industrial liquid waste, refuse derived fuel, sewerage, sewerage sludge, sludge from wastewater treatment, landfill gas, biogas, tires including end of life tires, or any combination thereof.
Embodiment 19. The process of any of embodiments 1 to 18 wherein the at least one material is selected from unsorted landfill waste, sorted landfill waste, tires, plastics, fibers, microbial biomass, waste wood, agriculture waste, forest waste, or combinations thereof.

The invention claimed is:
1. An integrated process comprising:
a) processing at least one of coal, refinery residues, petroleum coke, biomass, lignocellulosic material, black liquor, municipal solid waste, municipal liquid waste, industrial solid waste, industrial liquid waste, refuse derived fuel, sewerage, sewerage sludge, sludge from wastewater treatment, landfill gas, biogas, tires including end of life tires, unsorted landfill waste, sorted landfill waste, plastics, fibers, microbial biomass, waste wood, agriculture waste, forest waste, or any combination thereof in a gasification process, to produce a raw syngas steam comprising at least carbon monoxide and carbon dioxide, and to produce char byproduct;

b) passing at least a portion of the syngas stream to a gas fermentation process comprising a bioreactor containing a C1-fixing microorganism in a liquid nutrient medium to produce at least one alcohol fermentation product; and c) providing the at least one byproduct and the at least one fermentation product to a downstream operation to produce a tire.

2. The process of claim 1 wherein at least a second byproduct is produced by the gasification process and both the char byproduct and the second product are provided to the downstream operation to produce a tire.

3. The process of claim 1 wherein at least a second and a third byproduct are produced by the gasification process and the char byproduct, the second byproduct, and the third byproduct are provided for use in the downstream operation to produce a tire.

4. The process of claim 1 wherein at least a second, a third, and a fourth byproduct are produced by the gasification process and the char byproduct, the second byproduct, the third byproduct, and the fourth byproduct byproducts are provided for use in the downstream operation to produce a tire.

5. The process of claim 2 wherein the second byproduct of the gasification process is a metal or metal oxide comprising zinc.

6. The process of claim 1 further comprising processing the char byproduct to generate carbon black prior to being provided for use in the downstream operation to produce a tire.

7. The process of claim 1 wherein a second byproduct is produced by gasification process and the char byproduct and the second byproduct are provided to the same or different steps of the downstream operation to produce a tire.

8. The process of claim 1 wherein two or more byproducts are produced by the gasification process and the two or more byproducts are provided to the same or different steps of the downstream operation to produce a tire.

9. The process of claim 1 wherein the C1-fixing microorganism is an acetogenic carboxydotrophic microorganism.

10. The process of claim 1 wherein microorganism is selected from a genus of *Clostridium, Moorella, Carboxydothermus, Ruminococcus, Acetobacterium, Eubacterium, Butyribacterium, Oxobacter, Methanosarcina, Methanosarcina, Desulfotomaculum,* or *Cupriavidus.*

11. The process of claim 1 wherein the alcohol gas fermentation product and the char byproduct are provided to the same or different steps of the downstream operation to produce a tire.

* * * * *